United States Patent [19]

Kammann et al.

[11] Patent Number: 5,354,333
[45] Date of Patent: Oct. 11, 1994

[54] APPARATUS FOR IMPLANTING A FOLDING INTRAOCULAR LENS

[75] Inventors: Jochen Kammann; Ulrich Dretzler; Otmar Kanert, all of Dortmund, Fed. Rep. of Germany

[73] Assignee: adatomed Pharmazeutische und medizintechnische Gesellschaft mbH, Munich, Fed. Rep. of Germany

[21] Appl. No.: 979,368

[22] Filed: Nov. 20, 1992

Related U.S. Application Data

[63] Continuation of Ser. No. 727,938, Jul. 10, 1991, abandoned.

[30] Foreign Application Priority Data

Sep. 26, 1990 [DE] Fed. Rep. of Germany ....... 4030492

[51] Int. Cl.$^5$ ................................ A61F 2/16
[52] U.S. Cl. ........................ 623/6; 606/107
[58] Field of Search ............... 623/6; 606/107

[56] References Cited

U.S. PATENT DOCUMENTS

| 4,108,182 | 8/1978 | Hartman et al. |
| 4,474,073 | 10/1984 | Blaurock et al. ............ 74/424.8 |
| 4,681,102 | 7/1987 | Bartell ............................ 623/6 |
| 4,834,094 | 5/1989 | Patton et al. |
| 4,834,095 | 5/1989 | Miller. |

FOREIGN PATENT DOCUMENTS 2224214 2/1990 United Kingdom.

Primary Examiner—Randy C. Shay
Attorney, Agent, or Firm—Keck, Mahin & Cate

[57] ABSTRACT

An apparatus for implanting a folded intraocular lens of resilient material such as silicone lens comprises a tubular implantation instrument for carrying the folded lens therein, and a manipulator assembly which is connected to the implantation instrument and which comprises a pushing means for inserting the folded lens from the implantation instrument into the lens capsule of an eye.

3 Claims, 1 Drawing Sheet

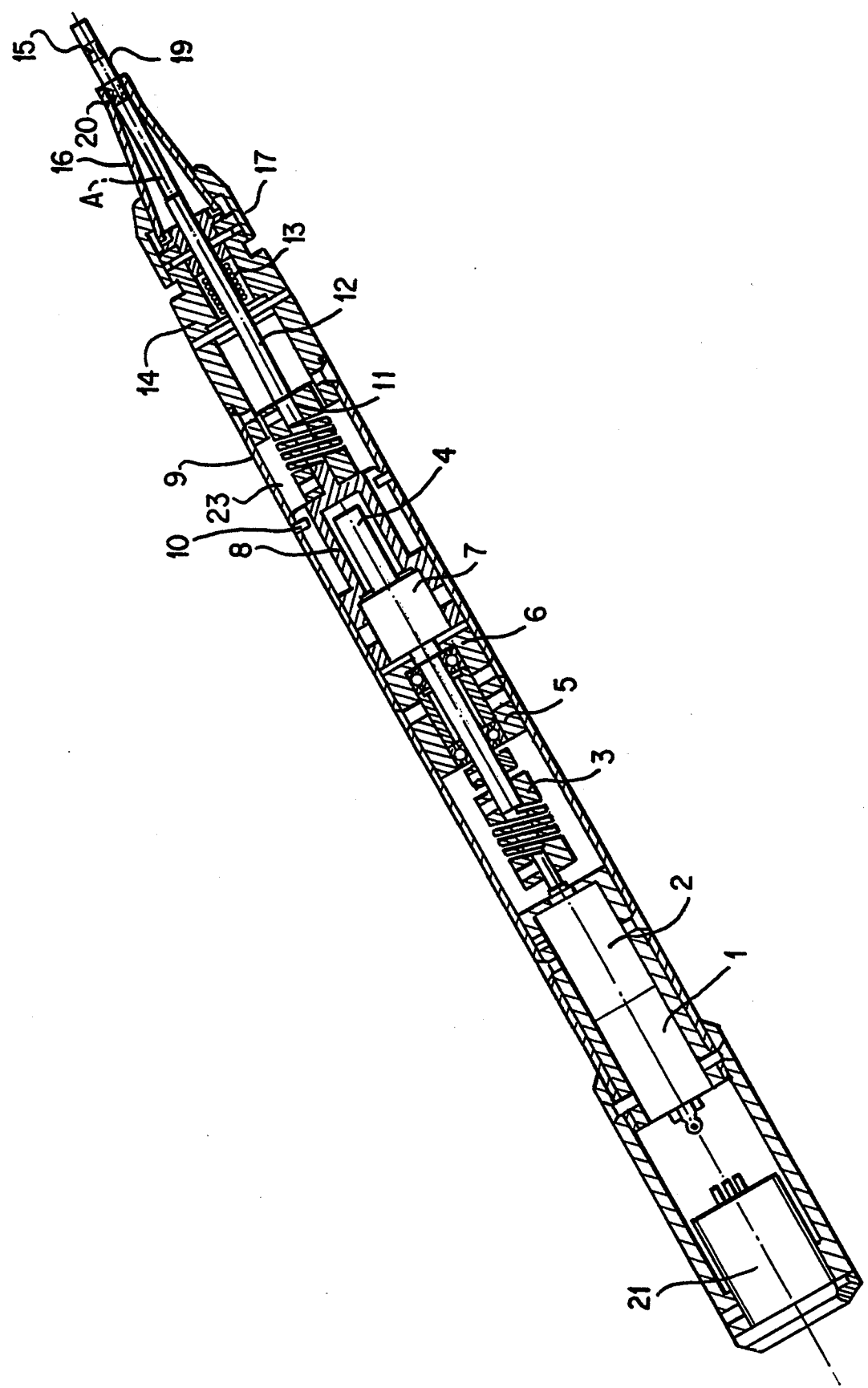

APPARATUS FOR IMPLANTING A FOLDING INTRAOCULAR LENS

This is a continuation of application Ser. No. 07/727,938, filed Jul. 10, 1991, abandoned.

BACKGROUND OF THE INVENTION

A cataract operation frequently involves inserting an intraocular lens of resilient material such as a silicone lens into the lens capsule of the eye which had been suffering from the cataract. However, it is found that handling an intraocular lens, in a folded condition, can often be a relatively difficult and laborious procedure. That is because it is necessary for the intraocular lens to be carefully folded so that it is only after it has been inserted into the lens capsule that it springs back into its original configuration, by virtue of its inherent resiliency, and thus appropriately fills and is positioned in the lens capsule of the eye. Hitherto that procedure involved using a tweezer instrument of a special configuration at its ends, for the purposes of inserting the folded intraocular lens into the lens capsule of the eye through the cut opening therein.

SUMMARY OF THE INVENTION

An object of the invention is to provide an apparatus for the implantation of a folded intraocular lens into the lens capsule of an eye, which ensures reliable handling of the intraocular lens upon insertion thereof when performing a cataract operation.

Another object of the present invention is to provide an apparatus for implanting a folded intraocular lens into a lens capsule of an eye, which is of a simple design configuration while being convenient to handle and easy and reliable in operation.

Still another object of the present invention is to provide an apparatus for implanting an intraocular lens into the lens capsule of an eye which can provide for enhanced accuracy of insertion of the intraocular lens and positioning thereof in the lens capsule.

Still a further object of the present invention is to provide an intraocular lens implantation apparatus which is specifically designed to afford controlled and accurate lens implantation.

In accordance with the principles of the present invention the foregoing and other objects are achieved by an apparatus for implanting a folded intraocular lens of resilient material, such as a silicone lens, comprising an implantation instrument of a tubular configuration with an inside diameter adapted to the folded lens, for insertion of the folded lens from the implantation instrument through a cut opening in the eye into the lens capsule of the eye. The apparatus further includes a manipulator means connected to the implantation instrument and including a pushing means aligned with the tubular interior of the implantation instrument, the pushing means being operable to displace the folded lens from the implantation instrument.

The apparatus configuration according to the invention can at least contribute to ensuring that the folded lens of resilient material is securely held in the interior of the tubular implantation instrument. The apparatus of the invention further advantageously provides that the folded lens is inserted into the lens capsule in a satisfactory fashion and with a specific guide action so that the lens can unfold within the lens capsule in its position therein and occupies the desired position in the lens capsule after the intraocular lens has unfolded into its original lens configuration. The operation of inserting the folded lens may be carried out in such a way that, after the intraocular lens has unfolded, the equator of the lens coincides with that of the lens capsule.

In order to deal with intraocular lenses of different dimensions and diameters, the tubular interior of the implantation instrument may be of different cross-sections and cross-sectional shapes. Preferably the implantation instrument may be in the form of a sterilisable storage container for the folded lens.

In another preferred feature of the invention, the implantation instrument is adapted to be secured to a housing of the manipulator by means of an adaptor insert, for example by means of a locking connection and/or a screw connection. For that purpose the adaptor insert may also be matched to the different cross-sections and cross-sectional configurations of the implantation instrument.

Preferably, the pushing means of the manipulator means comprises a push rod which is suitably guided in the longitudinal direction of the tubular implantation instrument. The push rod may provide for example a feed movement of about 10 millimetres. In order to provide that the folded intraocular lens which is disposed in the interior of the implantation instrument is handled carefully, in accordance with the invention a pushing or driving stem member which may comprise for example a soft material such as silicone rubber may be provided at the free end of the push rod, that is to say at the end thereof which is towards the implantation instrument, with the stem member being suitably matched to the cross-section of the tubular interior of the implantation instrument. The stem member is pushed into the implantation instrument by operation of the push rod to such an extent that the folded lens issues from the tubular interior of the implantation instrument and can then unfold in its position in the lens capsule.

For that purpose, the stem member may be disposed in the adaptor insert or it may be arranged in the tubular implantation instrument, particularly when the latter serves as a storage container for the folded lens.

The pushing or feed movement of the push rod which is guided exactly in the housing of the manipulator may be produced manually. In accordance with another preferred feature of the invention the manipulator means may include a rotary drive means which is thus operable to produce a uniform feed movement, for example at a fairly constant feed rate which may be for example of a maximum of about 1 millimetre per second. The rotary drive means may be more especially a dc voltage micromotor which affords a controllable speed of rotation. The rotary movement of the rotary drive means is converted by a transmission means disposed in the manipulator means into a longitudinal movement which is thus transmitted to the pushing means. That configuration can provide for highly precise insertion of the folded lens, while being simple to operate.

Further objects, features and advantages of the present invention will be apparent from the following description of a preferred embodiment thereof.

BRIEF DESCRIPTION OF THE DRAWING

The single FIGURE of the accompanying drawing is a view in longitudinal section of an embodiment of the apparatus according to the invention.

DESCRIPTION OF THE PREFERRED EMBODIMENT

Referring now to the drawing, shown therein in longitudinal section is an embodiment of an apparatus according to the invention for implanting a folded intraocular lens 15 of resilient material, such as a silicone lens, into the lens capsule of an eye, through a cut opening therein. The lens 15 is shown in a folded condition in an implantation instrument 19 which is of a generally tubular configuration. The inside diameter of the generally tubular configuration such as the implantation instrument 19 is suitably adapted to the dimensions such as the thickness and diameter or cross-sectional shape of the folded lens 15.

The implantation instrument 19 is inserted in a conical or tapering adaptor insert indicated at 16 which is connected to a manipulator which will be described in greater detail hereinafter. For the purposes of making that connection, the adaptor insert 16 has first and second claws 18 which can be arrested in a fixed position in a housing head portion 14 of the tubular housing 9 of the manipulator. The adaptor insert 16 is then definitively fixed to the housing 9 of the manipulator by means of a nut 17 which is fitted over the adaptor insert.

The manipulator includes a pushing arrangement comprising a push rod 12 and a driving or pushing stem member 20, which is guided displaceably in the head 14 of the housing 9 of the manipulator, in the longitudinal direction of the implantation instrument 19, that is to say, along a common axis as indicated at A. The push rod 12 is guided precisely in the head 14 of the housing 9 of the manipulator in the longitudinal direction as indicated by the axis A by means of a miniature ball bearing assembly as diagrammatically indicated at 13. The stem member 20 is disposed at and thus operatively associated with the front free end of the push rod 12, being the end thereof which is towards the implantation instrument 19. The stem member 20 may be disposed in the adaptor insert 16 or in the implantation instrument 19. The stem member 20 which is suitably matched to the cross-section of the tubular interior of the implantation instrument 19 comprises a soft material so as to ensure that the folded intraocular lens 15 is handled carefully when it is displaced in the implantation instrument 19. It will be seen from the drawing that the push rod 12, the stem member 20 and the folded lens 15 are aligned relative to each other along the axis A.

In order to produce the feed movement of the push rod 12, the manipulator illustrated has a rotary drive means which more especially is shown in the form of an electric motor and more particularly in the illustrated embodiment in the form of a dc voltage micromotor as indicated at 1, which is controllable in respect of its speed of rotation. Reference numeral 21 at the left-hand end of the manipulator illustrated in the drawing identifies a battery for powering the micromotor 1.

The micromotor 1 is drivingly coupled to a planetary transmission as indicated diagrammatically by reference numeral 2. The drive motion from the micromotor 1, which is transmitted by way of the transmission 2, is thus passed by way of a coupling 3 which is connected to the planetary transmission 2 and which is preferably in the form of a helix type coupling to a spindle 4 which in the illustrated embodiment is in the form of a miniature ball roller spindle so that the spindle 4 is driven in rotation.

The spindle 4 is mounted in an overhung relationship in a bearing housing 6 by way of two ball bearing assemblies 5, more especially radial deep-groove ball bearings, and is secured in the axial direction of the spindle. The bearing housing 6 is held fast by screw means on the tubular housing 9 of the manipulator.

For the purposes of conversion of the rotary movement of the spindle 4 into a longitudinal movement, the spindle 4 is a component of a spindle-nut drive assembly as indicated at 22. For that purpose the spindle 4 is guided in a ball nut 7 of the drive assembly 22. The nut 7 is screwed to a sleeve 8 which in turn is longitudinally guided in the tubular housing 9 of the manipulator, by means of pins 10. To provide the guidance action, the pins 10 project into the interior of the tubular housing 9 of the manipulator and engage into longitudinally extending slots 23 in the sleeve 8. Thus, when the micromotor 1 is operated, the result is that the spindle 4 is driven in rotation and a portion of the spindle 4 which is suitably guided in a female screwthread in the nut 7 causes the nut 7 to be displaced with a longitudinal movement within the housing 9 of the manipulator, thereby converting the rotary movement of the spindle 4 into a longitudinal movement. That longitudinal movement of the nut 7 is thus transmitted to the sleeve 8 which is similarly displaced within the tubular housing 9 in the longitudinal direction, that is to say in the direction indicated by the axis A, with the sleeve 8 being guided by the co-operation of the slots 23 therein with the fixed pins 10.

The linear movement of the sleeve 8 in the axial direction as indicated by A is transmitted by way of a further coupling 11 which is also preferably in the form of a helix-type coupling to the push rod 12 which, as indicated above, is suitably mounted in the head 14 of the housing by way of the miniature ball bearing assembly 13.

The push rod 12 can be moved in a forward direction, that is to say towards the right in the drawing, at a maximum feed speed of for example of about 1 millimeter per second, so that during that movement the folded intraocular lens 15 is pushed into the lens capsule of the eye by being ejected from the implantation instrument 19.

The rearward movement of the push rod 12, after insertion of the lens 15 into the lens capsule of an eye, is effected by reversing the direction of rotation of the motor 1. When that happens, the push rod 12 is returned to its starting position.

The manipulator is preferably designed to be steam-sterilisable, for which purpose all passage openings therein are preferably sealed by O-ring seals.

The overall longitudinal dimension of the apparatus illustrated in the drawing is about 215 millimeters. The length of the implantation instrument 19, which projects out of the adaptor insert 16, is about 10 millimeters. Accordingly the feed travel S of the push rod 12 is also about 10 millimeters. The length of the adaptor insert 16 which is fitted on to the manipulator, together with the implantation instrument 19, is about 27 millimeters while the diameter of the manipulator in the region of the battery 21 is about 20 millimeters. It will be appreciated that those dimensions are given by way of example of a specific embodiment of the apparatus.

It will further be appreciated that the above-described construction has been set forth solely by way of example and illustration of the principles of the present invention and that various modifications and alterations may be made therein without thereby departing from the spirit and scope of the present invention.

What is claimed is:

1. Apparatus for implanting an intraocular lens of resilient material in the lens capsule of an eye combined with the intraocular lens being implanted, comprising:

a tubular housing having a front end and a rear end;

a push rod means disposed in the housing slidably in a longitudinal direction thereof and having first and second ends, the first end being disposed towards the front end of said housing;

an electrical rotary drive means disposed in the housing, for generating rotary movement;

a spindle-nut drive assembly including a spindle upon which the rotary movement is transmitted and which is guided in a female screw thread of a nut, said nut being screwed to a sleeve in said housing, thereby converting the rotary movement into a longitudinal movement of the sleeve;

guidance means for longitudinal movement of the sleeve in the tubular housing;

transmitting means for transmitting the longitudinal movement of the sleeve to the push rod means;

an implantation instrument mounted to said front end of said housing, said implantation instrument accommodating an intraocular lens therein in a folded condition, in alignment with said push rod means; and a stem member operatively associated with said first end of said push rod means and adapted to displace said folded intraocular lens from said implantation instrument by displacement of said push rod means toward said front end of said housing.

2. Apparatus as set forth in claim 1 and further including an adaptor insert connected to said housings adapted to secure the implantation instrument to said housing.

3. Apparatus as set forth in claim 1 wherein said implantation instrument is in the form of a sterilizable storage container for a lens.

* * * * *